United States Patent
Mayer et al.

(10) Patent No.: US 6,849,761 B2
(45) Date of Patent: Feb. 1, 2005

(54) SUBSTITUTED NAPHTHOIC ACID DERIVATIVES USEFUL IN THE TREATMENT OF INSULIN RESISTANCE AND HYPERGLYCEMIA

(75) Inventors: Scott Christian Mayer, Bridgewater, NJ (US); Alan Howard Katz, Lawrenceville, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/656,981

(22) Filed: Sep. 5, 2003

(65) Prior Publication Data

US 2004/0127570 A1 Jul. 1, 2004

Related U.S. Application Data

(60) Provisional application No. 60/408,314, filed on Sep. 5, 2002.

(51) Int. Cl.[7] .............................................. C07C 229/00
(52) U.S. Cl. ........................................ 562/451; 514/567
(58) Field of Search ........................... 562/451; 514/567

(56) References Cited

U.S. PATENT DOCUMENTS

| | | |
|---|---|---|
| 6,001,884 A | 12/1999 | Nemeth et al. |
| 6,031,003 A | 2/2000 | Nemeth et al. |
| 6,143,789 A | 11/2000 | Lefoulon et al. |
| 6,211,244 B1 | 4/2001 | Van Wagenen et al. |

FOREIGN PATENT DOCUMENTS

| | | |
|---|---|---|
| JP | 2000-178243 | 6/2000 |
| WO | WO 95/11221 | 4/1995 |
| WO | WO 00/21920 | 4/2000 |

OTHER PUBLICATIONS

Reaven, et al., "Nonketotic Diabetes Mellitus: Insulin Deficiency or Insulin Resistance?", American Journal of Medicine, (Jan. 1976), vol. 60, pp 80–88.
Stout, Metabolism: Clinical & Experimental, (Dec. 1985), 34 (12 Suppl 1): 7–12, (Abstract).
Pyorala, et al., Diabetes/Metabolism Reviews, "Diabetes and Atherosclerosis: An Epidemiologic View", (1987), vol. 3, pp 463–524.
Jarrett, R.J., et al Diabetes/Metabolism Review, "Cardiovascular Disease and Hypertension in Diabetes Mellitus", (1989), vol. 5, No 7, 547–558.
Harris, et al., Diabetes in America, "Mortality From Diabetes", Chapter 29, pp 1–48, (1985).
Defronzo and Ferrannini, Diabetes Care, "Insulin resistance-.",(Mar. 1991), 14, 173–194 (Abstract).
Haring, Diabetalogia, "The insulin receptor: signalling mechanism and contribution to the pathogenesis of insulin resistance", (1991), 34, 848–861 (Abstract).

B.J. Goldstein, J. Cellular Biochemistry, "Protein–tyrosine phosphatases and the regulation of insulin action", (1992), 48, 33 (Abstract).
B.J. Goldstein, Receptor , "Reg. of insulin receptor signaling by protein–tyrosine dephosphorylation", (1993), 3, 1–15 (Abstract).
F. Ahmad and B.J. Goldstein Biochim. Biophys Acta , "Purification, identification and subcellular distribution of three predominant protein–tyrosine phosphatase enzymes in skeletal muscle tissue", (1995), 1248, 57–69 (Abstract).
McGuire, et al., Diabetes, "Abnormal Regulation of Protein Tyrosine Phosphatase Activities in Skeletal Muscle of Insulin–Resistant Humans", (1991), vol. 40, 939–942.
Meyerovitch, et al., J. Clinical Invest., "Hepatic phosphotyrosine phosphatase activity and its alterations in diabetic rats", (1989), vol. 84, 976–983 (Abstract).
Sredy, et al Metabolism: Clinical & Experimental, "Insulin resistance is associated with abnormal dephosphorylation of a synthetic phosphopeptide corresponding to the major autophosphorylation sites of the insulin receptor", 44, 1074–1081 1995 (Abstract).

*Primary Examiner*—Paul J. Killos

(57) ABSTRACT

This invention provides compounds of Formula I having the structure

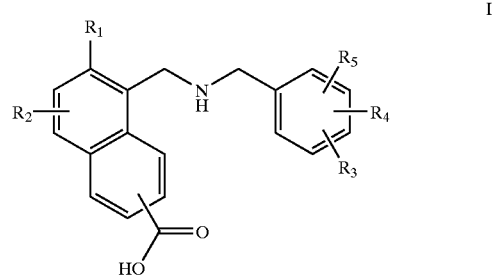

wherein:

$R_1$ is hydroxyl, alkoxy of 1–4 carbons or —$O(CH_2)_n X$;
n is an integer of 1–13;
X is $CONHR_6$ or $CO_2 R_6$;
$R_2$ is hydrogen, halogen, hydroxyl, alkyl of 1–4 carbons, alkoxy of 1–4 carbons or acyl of 1–4 carbons;
$R_3$, $R_4$ and $R_5$ are each independently, hydrogen, halogen, hydroxyl, alkyl of 1–4 carbons, alkoxy of 1–4 carbons, acyl of 1–4 carbons, $CF_3$, $OCF_3$, $SO_2 NHR_6$, $NR_6 R_7$ or $CO_2 R_6$;
$R_6$, and $R_7$ are each independently, hydrogen, alkyl of 1–4 carbons, or alkylaryl where the aryl group is substituted with $R_2$;

or a pharmaceutically acceptable salt thereof, which are useful in treating metabolic disorders related to insulin resistance or hyperglycemia.

12 Claims, No Drawings

SUBSTITUTED NAPHTHOIC ACID DERIVATIVES USEFUL IN THE TREATMENT OF INSULIN RESISTANCE AND HYPERGLYCEMIA

This application claims priority from co-pending provisional application Ser. No. 60/408,314 filed on Sep. 5, 2002 the entire disclosure of which is hereby incorporated by reference.

FIELD OF THE INVENTION

This invention relates to substituted naphthoic acid derivatives as inhibitors of protein-tyrosine phosphatases (PTPases) and therapeutic compositions containing such compounds useful in the treatment of insulin resistance associated with obesity, glucose intolerance, diabetes mellitus, hypertension and ischemic diseases of the large and small blood vessels.

BACKGROUND OF THE INVENTION

The prevalence of insulin resistance in glucose intolerant subjects has long been recognized. Reaven et al (*American Journal of Medicine* 1976, 60, 80) used a continuous infusion of glucose and insulin (insulin/glucose clamp technique) and oral glucose tolerance tests to demonstrate that insulin resistance existed in a diverse group of nonobese, nonketotic subjects. These subjects ranged from borderline glucose tolerant to overt, fasting hyperglycemia. The diabetic groups in these studies included both insulin dependent (IDDM) and noninsulin dependent (NIDDM) subjects. Coincident with sustained insulin resistance is the more easily determined hyperinsulinemia, which can be measured by accurate determination of circulating plasma insulin concentration in the plasma of subjects. Hyperinsulinemia can be present as a result of insulin resistance, such as is in obese and/or diabetic (NIDDM) subjects and/or glucose intolerant subjects, or in IDDM subjects, as a consequence of over injection of insulin compared with normal physiological release of the hormone by the endocrine pancreas.

The association of hyperinsulinemia with obesity and with ischemic diseases of the large blood vessels (e.g. atherosclerosis) has been well established by numerous experimental, clinical and epidemiological studies (summarized by Stout, *Metabolism* 1985, 34, 7, and in more detail by Pyorala et al, *Diabetes/Metabolism Reviews* 1987, 3, 463). Statistically significant plasma insulin elevations at 1 and 2 hours after oral glucose load correlates with an increased risk of coronary heart disease.

Since most of these studies actually excluded diabetic subjects, data relating the risk of atherosclerotic diseases to the diabetic condition are not as numerous, but point in the same direction as for nondiabetic subjects (Pyorala et al). However, the incidence of atherosclerotic diseases in morbidity and mortality statistics in the diabetic population exceeds that of the nondiabetic population (Pyorala et al; Jarrett *Diabetes/Metabolism Reviews* 1989,5, 547; Harris et al, *Diabetes in America*, Chapter 29, pp 1–48, 1985.)

The independent risk factors obesity and hypertension for atherosclerotic diseases are also associated with insulin resistance. Using a combination of insulin/glucose clamps, tracer glucose infusion and indirect calorimetry, it has been demonstrated that the insulin resistance of essential hypertension is located in peripheral tissues (principally muscle) and correlates directly with the severity of hypertension (DeFronzo and Ferrannini, *Diabetes Care* 1991, 14, 173). In hypertension of the obese, insulin resistance generates hyperinsulinemia, which is recruited as a mechanism to limit further weight gain via thermogenesis, but insulin also increases renal sodium reabsorption and stimulates the sympathetic nervous system in kidneys, heart, and vasculature, creating hypertension.

It is now appreciated that insulin resistance is usually the result of a defect in the insulin receptor signaling system, at a site post binding of insulin to the receptor. Accumulated scientific evidence demonstrating insulin resistance in the major tissues which respond to insulin (muscle, liver, adipose), strongly suggests that a defect in insulin signal transduction resides at an early step in this cascade, specifically at the insulin receptor kinase activity, which appears to be diminished (reviewed by Haring, *Diabetalogia* 1991, 34, 848).

Protein-tyrosine phosphatases (PTPases) play an important role in the regulation of phosphorylation of proteins. The interaction of insulin with its receptor leads to phosphorylation of certain tyrosine molecules within the receptor protein, thus activating the receptor kinase. PTPases dephosphorylate the activated insulin receptor, attenuating the tyrosine kinase activity. PTPases can also modulate post-receptor signaling by catalyzing the dephosphorylation of cellular substrates of the insulin receptor kinase. The enzymes that appear most likely to closely associate with the insulin receptor and therefore, most likely to regulate the insulin receptor kinase activity, include PTP1B, LAR, PTPα and SH-PTP2 (B. J. Goldstein, *J. Cellular Biochemistry* 1992, 48, 33; B. J. Goldstein, *Receptor* 1993, 3, 1–15,; F. Ahmad and B. J. Goldstein *Biochim. Biophys Acta* 1995, 1248, 57–69).

McGuire et al. (*Diabetes* 1991, 40, 939), demonstrated that nondiabetic glucose intolerant subjects possessed significantly elevated levels of PTPase activity in muscle tissue vs. normal subjects, and that insulin infusion failed to suppress PTPase activity as it did in insulin sensitive subjects.

Meyerovitch et al (*J. Clinical Invest.* 1989, 84, 976) observed significantly increased PTPase activity in the livers of two rodent models of IDDM, the genetically diabetic BB rat, and the STZ-induced diabetic rat. Sredy et al (*Metabolism*, 44, 1074, 1995) observed similar increased PTPase activity in the livers of obese, diabetic ob/ob mice, a genetic rodent model of NIDDM.

U.S. Pat. No. 6,211,244-B1 discloses aryl substituted amine derivatives of the following formula which are useful as inorganic ion receptor modulators for inhibition of bone resorption and treatment of hyperparathyroidism, Paget's disease, hypercalcemic disorders, osteoporosis, hypertension, and renal dystrophy.

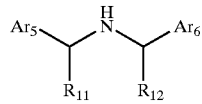

U.S. Pat. No. 6,211,244-B1 claims that at least one of $R_{11}$ or $R_{12}$ is methyl, and $Ar_5$ does not specifically contain a naphthoic acid.

U.S. Pat. No. 6,031,003 discloses substituted 1-naphthylmethyl-benzyl examines derivatives of the following formula which are useful for treating disorders bv modulating calcium receptor activity in vitro by administering a calcimimetic, or a calcilytic compound. U.S. Pat. No. 6,031,003 discloses at least one benzylic methyl group substitution, and when two X's equal a fused aromatic group, the patent does not specifically claim a naphthoic acid.

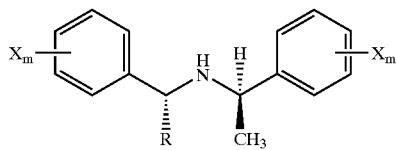

U.S. Pat. No. 6,001,884 discloses diarylmethylamine derivatives of the following formula useful for the treatment of abnormal calcium homeostasis associated with hyperparathyroidism, hypertension, and osteoporosis. U.S. Pat. No. 6,001,884 discloses at least one benzylic methyl group substitution, and when X+X or Y+Y equals a fused aromatic group, the patent does not specifically claim a naphthoic acid.

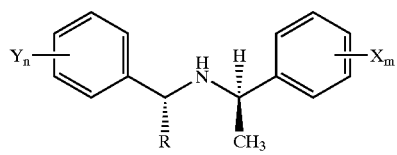

JP 2000178243 discloses biphenylamidine derivatives of the following formula which are inhibitors of blood coagulation and are useful for preventing and treating thrombosis and embolism. JP 2000178243 discloses that the structure specifically contains amidino group ($A_1$), $Y_1$ does not specifically contain a naphthoic acid, and m,n are undefined.

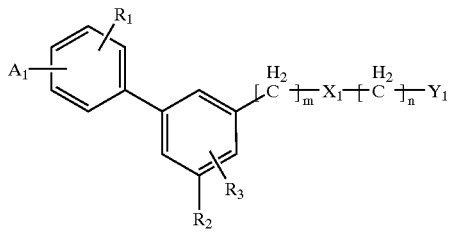

WO 200021920 discloses diaminopropionic acid derivatives of the following formula which are useful as ICAM-1 (intracellular adhesion molecule-1) antagonists for the treatment of rheumatoid arthritis, psoriasis, multiple sclerosis, Crohn's disease, and ischemic reperfusion injury. WO 200021920 claims that $R_1$ can be a substituted naphthylene and $R_2$ can be a methylene-amide linkage.

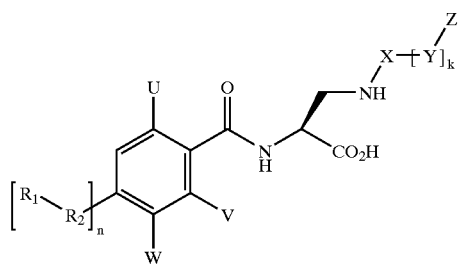

EP 0919541-A1 discloses naphthalenic compounds of the following formula which are melatonin receptor agonists and antagonists useful in the treatment of circadian rhythm disorders, seasonal depression, cardiovascular disorders, appetite disorders, and obesity. EP 0919541-A1 claims that $G_2$ is either an amide, thioamide, urea, or thiourea.

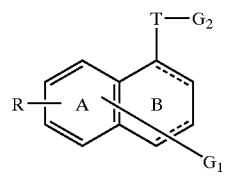

WO 9511221 discloses arylalkylamine derivatives of the following formula which are useful as inorganic ion receptor modulators for treating diseases or disorders by altering inorganic ion receptor activity, preferably calcium receptor activity. WO 9511221 discloses at least one benzylic methyl group substitution, and when two X's equal a fused aromatic group, the patent does not specifically claim a naphthoic acid.

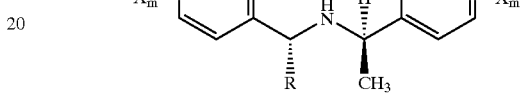

The compounds of this invention have been shown to inhibit PTPases derived from human-derived recombinant PTPase-1B (hPTP-1B) in vitro. They are useful in the treatment of insulin resistance associated with obesity, glucose intolerance, diabetes mellitus, hypertension and ischemic diseases of the large and small blood vessels.

SUMMARY OF THE INVENTION

The present invention comprises compounds of Formula I:

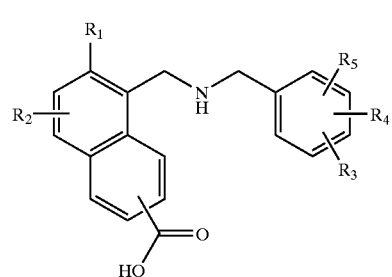

wherein:

$R_1$ is hydroxyl, alkoxy of 1–4 carbons or —O(CH$_2$)$_n$X;
n is an integer of 1–3;
X is CONHR$_6$ or CO$_2$R$_6$;
$R_2$ is hydrogen, halogen, hydroxyl, alkyl of 1–4 carbons, alkoxy of 1–4 carbons or acyl of 1–4 carbons;
$R_3$, $R_4$ and $R_5$ are each independently, hydrogen, halogen, hydroxyl, alkyl of 1–4 carbons, alkoxy of 1–4 carbons, acyl of 1–4 carbons, CF$_3$, OCF$_3$, SO$_2$NHR$_6$, NR$_6$R$_7$, or CO$_2$R$_6$;
$R_6$, and $R_7$ are each, independently, hydrogen, alkyl of 1–4 carbons, or alkylaryl where the aryl group is substituted with $R_2$;

or a pharmaceutically acceptable salt thereof.

The present compounds are useful in treating metabolic disorders related to insulin resistance or hyperglycemia.

DETAILED DESCRIPTION OF THE INVENTION

As used herein, "alkyl" includes both straight chain as well as branched moieties. As used herein "halogen" means bromine, chlorine, fluorine, and iodine.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains a carboxylate or phenolic moiety, or similar moiety capable of forming base addition salts.

The compounds of this invention may contain an asymmetric carbon atom and some of the compounds of this invention may contain one or more asymmetric centers and may thus give rise to optical isomers and diastereomers. While shown without respect to stereochemistry in Formula I, the present invention includes such optical isomers and diastereomers, as well as the racemic and resolved, enantiomerically pure R and S stereoisomers, as well as other mixtures of the R and S stereoisomers and pharmaceutically acceptable salts thereof.

A preferred form of the compounds of this invention are those of Formula II:

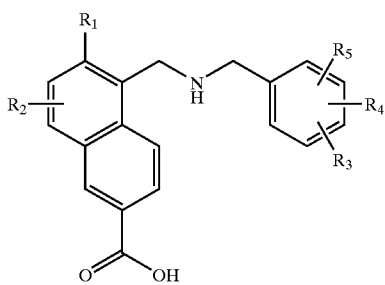

wherein $R_1$, n, X, $R_2$, $R_3$, $R_4$, $R_5$, $R_6$, and $R_7$ are defined as above with respect to Formula I, or a pharmaceutically acceptable salt thereof.

A more preferred form of the compounds of this invention are those of Formula III:

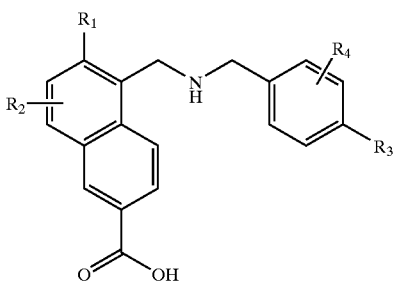

wherein:

$R_1$ is hydroxyl, alkoxy of 1–4 carbons, or —O(CH$_2$)$_n$CO$_2$R$_5$;

n is an integer of 1–3;

$R_2$ is hydrogen, halogen, hydroxyl, alkyl of 1–4 carbons, alkoxy of 1–4 carbons, or acyl of 1–4 carbons;

$R_3$ and $R_4$ are each, independently, hydrogen, halogen, hydroxyl, alkyl of 1–4 carbons, alkoxy of 1–4 carbons, acyl of 1–4 carbons, $CF_3$, $OCF_3$, $SO_2NHR_5$, $NR_5R_6$, or $CO_2R_5$;

$R_5$ and $R_6$ are each, independently, hydrogen, alkyl of 1–4 carbons, or alkylaryl where the aryl group is substituted with $R_2$;

or a pharmaceutically acceptable salt thereof.

The most preferred compounds of this invention are:

6-Methoxy-5-({[4-(trifluoromethoxy)benzyl]amino}methyl)-2-naphthoic acid, or a pharmaceutically acceptable salt thereof;

5-{[(4-Fluorobenzyl)amino]methyl}-6-methoxy-2-naphthoic acid, or a pharmaceutically acceptable salt thereof;

5-({[4-(Aminosulfonyl)benzyl]amino}methyl)-6-methoxy-2-naphthoic acid, or a pharmaceutically acceptable salt thereof;

5-({[4-(Dimethylamino)benzyl]amino}methyl)-6-methoxy-2-naphthoic acid, or a pharmaceutically acceptable salt thereof; and 6-(Carboxymethoxy)-5-({[4-(trifluoromethoxy)benzyl]amino}methyl)-2-naphthoic acid, or a pharmaceutically acceptable salt thereof.

The compounds of this invention can be readily prepared according to the following schemes from commercially available starting materials or starting materials which can be prepared using literature procedures. These schemes show the preparation of representative compounds of this invention. It is also possible to make use of variants of these process steps, which in themselves are known to and well within the preparatory skill of the medicinal chemist. In the following reaction schemes, $R_1$, $R_2$, $R_3$, $R_4$, and $R_5$ are selected from groups defined above.

In Scheme I (when $R_1$=MeO), substituted naphthoic acids (1) are first protected as their methyl esters using TMS diazomethane as the reagent. The intermediate esters are formylated using POCl$_3$ in DMF; the aldehyde functionalities are generated ortho to the methoxy substituent to afford only compounds 2. A reductive amination reaction involving sodium cyanoborohydride and substituted benzyl amines incorporates secondary amino groups into these molecules. After hydrolysis under basic conditions, acids 3 are produced.

Scheme I

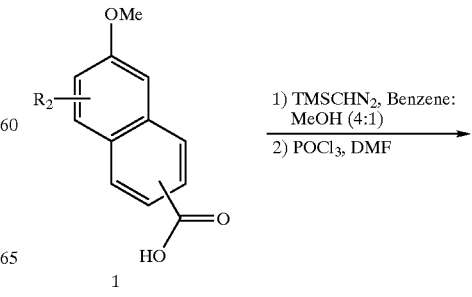

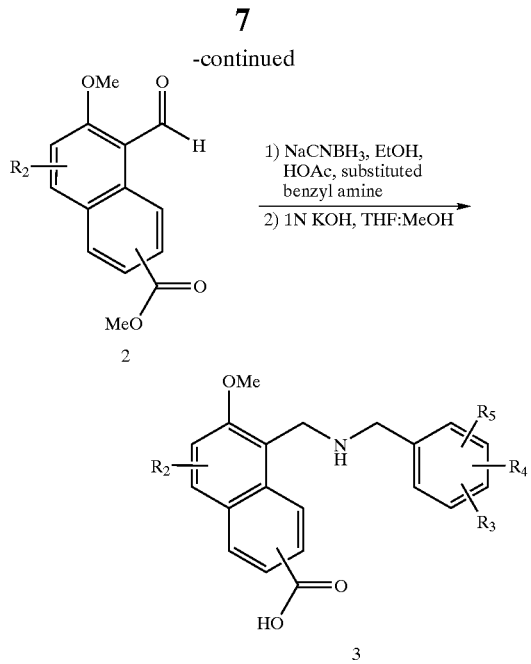

In Scheme II (when $R_1$=OH), substituted naphthoic acids (4) are again protected as their methyl esters using TMS diazomethane as the reagent. The intermediate esters in these cases are alkylated at the phenolic oxygen using reagents such as methyl bromo acetate under basic conditions to generate compounds 5 (bromo acetonitrile can be used instead to generate amides after oxidation). Esters 5 are then formylated using $POCl_3$ in DMF; the aldehyde functionalities are again generated ortho to the alkoxy substituent. A reductive amination reaction involving sodium cyanoborohydride and substituted benzyl amines incorporates secondary amino groups into these molecules. After hydrolysis under basic conditions, acids 6 are produced.

Scheme II

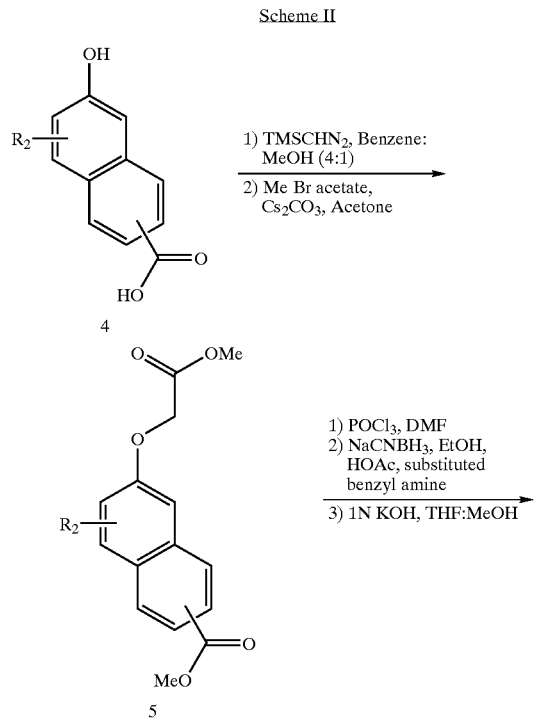

The compounds of this invention are useful in treating metabolic disorders related to insulin resistance or hyperglycemia, typically associated with obesity or glucose intolerance. The compounds of this invention are therefore, particularly useful in the treatment or inhibition of type II diabetes. The compounds of this invention are also useful in modulating glucose levels in disorders such as type I diabetes.

The ability of compounds of this invention to treat or inhibit disorders related to insulin resistance or hyperglycemia was established with representative compounds of this invention in the following standard pharmacological test procedure which measures the inhibition of PTPase.

Inhibition Assay

Measurement of PTPase activity: Compounds are assayed in an enzyme activity-based assay. PTP-1B is known to dephosphorylate phosphopeptides. This assay is a fluorescence intensity based kinetic assay, taking advantage of a non-peptidyl substrate, 6,8-difluoro-4-methylumbelliferyl phosphate (DIFMUP). When excited at 358 nm, the dephosphorylated product of DIFMUP emits at 450 nm.

Examples 1–5 (set forth below) were analyzed as follows. The assay was conducted in black 384-well non-treated plates (Costar#3710). The assay buffer contained 50 mM 3,3-dimethyl glutaric acid, pH 7.0, 48 mM NaCl, 1 mM EDTA. Inhibitors were prepared as DMSO solution and diluted to desired concentrations using 50 mM HEPES, pH 7.4. PTP-1B was diluted to a 2.5 nM working stock using the assay buffer containing additional 0.001% (w/v) hydrogenated Triton X-100. DIFMUP was diluted to 40 $\mu$M using the assay buffer. 5 $\mu$l of inhibitor was first dispensed into assay plate. In cases of control reactions, 5 $\mu$l of the assay buffer was dispensed. This was followed by 25 $\mu$l of DIFMUP working stock. The reaction was then initiated by the addition of 20 $\mu$l of PTP-1B working stock. The final DIFMUP concentration was 20 $\mu$M (~1.6×$K_m$). The final enzyme concentration was 1 nM and the detergent concentration was 0.0004% (w/v). Typical inhibitor concentrations were from 0.08 to 40 $\mu$M. The reaction progress was monitored continuously for 30 min.

Calculations: For data analysis, the last five data points were used to obtain a slope corresponding to the estimated steady-state velocity ($V_s$), and the overall progress curves were used to obtain the average velocity ($V_a$), by linear regression in both cases. The apparent final potency of inhibitor ($K_{iapp}$) was then calculated from $V_s$ data, using the standard hyperbolic inhibition equation. The $IC_{50}$ values were calculated from $V_a$ data using the sigmoidal inhibition equation. % inhibition values were calculated from $V_a$ values of inhibitor at 40 $\mu$M, and the average $V_a$ value of control reactions. The results are set forth in Table 1 below:

TABLE 1

| Example | PTP-1B activity (% Inhibition @ 40 μM) |
|---|---|
| 1 | 50 |
| 2 | 37 |
| 3 | 23 |
| 4 | 34 |
| 5 | 38 |

Based on the results obtained in the standard pharmacological test procedure, the compounds of this invention were shown to inhibit PTPase activity and were therefore useful in treating metabolic disorders related to insulin resistance or hyperglycemia, typically associated with obesity or glucose intolerance. More particularly, the compounds of this invention are useful in the treatment or inhibition of type II diabetes, and in modulating glucose levels in disorders such as type I diabetes. As used herein, the term modulating means maintaining glucose levels within clinically normal ranges.

Effective administration of the compounds of this invention may be given at a daily dosage of from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, , xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s). Suppository formulations may be made from traditional materials, including cocoa butter, with or without the addition of waxes to alter the suppository's melting point, and glycerin. Water soluble suppository bases, such as polyethylene glycols of various molecular weights, may also be used.

It is understood that the dosage, regimen and mode of administration of these compounds will vary according to the malady and the individual being treated and will be subject to the judgment of the medical practitioner involved.

It is preferred that the administration of one or more of the compounds herein begin at a low dose and be increased until the desired effects are achieved.

The following procedures describe the preparation of representative examples of this invention.

EXAMPLE 1

6-Methoxy-5-({[4-(trifluoromethoxy)benzyl]amino}methyl)-2-naphthoic acid step 1

6-Methoxy-2-naphthoic acid methyl ester

To a stirred solution of 6-methoxy-2-naphthoic acid (10.0 g, 49.5 mmol) in benzene:MeOH (4:1, 200 mL) at 0° C. was added TMS diazomethane (29.7 mL, 2.0 M in hexnae, 59.4 mmol) dropwise. After initial addition of reagent, TLC showed reaction was not quite complete, so another 4 mL of TMS diazomethane added. The reaction was then stirred for 1 h before total completion. After concentration, the residue was recrystallized from MeOH:H$_2$O to afford the product (8.67 g, 81%) as a solid; $^1$H NMR (DMSO-d$_6$) δ3.85 (s, 3H), 3.87 (s, 3H), 7.22 (dd, J=2.6, 9.0 Hz, 1H), 7.37 (d, J=2.4 Hz, 1H), 7.85–7.92 (m, 2H), 8.00 (d, J=9.0 Hz, 1H), 8.51 (s, 1H); mass spectrum [(+) ESI], m/z 217 (M+H)$^+$.

step 2

6-Methoxy-5-formyl-2-naphthoic acid methyl ester

To a stirred solution of 6-methoxy-2-naphthoic acid methyl ester (10.3 g, 47.6 mmol) in DMF (36.9 mL, 476 mmol) at 5° C. was added POCl$_3$ (44.4 mL, 476 mmol) dropwise. The reaction mixture was heated to 80° C. After 2 days at this temperature, the reaction was poured into ice/H$_2$O (400 mL). The solution was made basic with addition of solid Na$_2$CO$_3$. The resulting mixture was extracted with EtOAc (2×400 mL). The organic layer was washed with brine (80 mL) and dried (MgSO$_4$). After concentration, the residue was recrystallized from MeOH:H$_2$O to afford the product (7.30 g, 63%) as a solid; $^1$H NMR (DMSO-d$_6$) δ3.91 (s, 3H), 4.11 (s, 3H), 7.72 (d, J=9.3 Hz, 1H), 8.10 (dd, J=2.0, 9.0 Hz, 1H), 8.53 (d, J=9.2 Hz, 1H), 8.66 (d, J=1.8 Hz, 1H), 9.17 (d, J=9.0 Hz, 1H), 10.76 (s, 1H).

step 3

6-Methoxy-5-({[4-(trifluoromethoxy)benzyl]amino}methyl)-2-naphthoic acid methyl ester To a stirred solution of 6-methoxy-5-formyl-2-naphthoic acid methyl ester (1.09 g, 4.46 mmol) in EtOH (40 mL) at room temperature was added 4-trifluoromethoxy-benzyl amine (0.749 mL, 4.91 mmol) followed by HOAc (0.255 mL, 4.46 mmol). After 10 min. at this temperature, sodium cyanoborohydride (0.420 g, 6.69 mmol) was added, and reaction was continued stirring at rt for 4 h. After 1 h at this temperature, the reaction was heated to 45° C. for 2 h. The solution was quenched with sat. aq. NaHCO$_3$ (20 mL) and then extracted with EtOAc (200 mL). The organic layer was washed with brine (20 mL) and dried (MgSO$_4$). After concentration, the residue was purified by flash chromatography (0 to 10% MeOH:CHCl$_3$ gradient) to afford the product (0.780 g, 42%) as a solid; $^1$H NMR (DMSO-d$_6$) δ3.77 (s, 2H), 3.86 (s, 3H), 3.88 (s, 3H), 4.07 (s, 2H), 7.26 (d, J =8.0 Hz, 2H), 7.44 (d, J=8.6 Hz, 2H), 7.48 (d, J=9.2 Hz, 1H), 7.88 (dd, J=1.9, 8.9 Hz, 1H), 8.06 (d, J=5.2 Hz, 1H), 8.08 (d, J=5.3 Hz, 1H), 8.52 (d, J=1.7 Hz, 1H); mass spectrum [(+) EI], m/z 420 (M+H)$^+$.

step 4

6-Methoxy-5-({[4-(trifluoromethoxy)benzyl]amino}methyl)-2-naphthoic acid

To a stirred solution of 6-methoxy-5-({[4-(trifluoromethoxy)-benzyl]amino}methyl)-2-naphthoic acid methyl ester (0.286 g, 0.682 mmol) in THF (1.00 mL) at rt was added 1 N KOH (0.682 mL, 0.682 mmol) dropwise. Enough MeOH (~0.500 mL) was added to make reaction homogeneous. After 1 h at this temperature, the reaction was heated to 45° C. for 2 h. The solution was diluted with $H_2O$ (~2–3 mL) and then acidified to pH 1 with 2 N HCl. The resulting solid was filtered off, washed with $H_2O$ and hexane, and dried on the high vacuum for 18 h to afford the product (0.207 g, 69%) as a white solid, mp 235–237° C.; $^1$H NMR (DMSO-$d_6$) δ3.94 (s, 3H), 4.33 (s, 2H), 4.52 (s, 2H), 7.47 (d, J=8.3 Hz, 2H), 7.59 (d, J=9.2 Hz, 1H), 7.71 (d, J=8.4 Hz, 2H), 7.99 (d, J=9.0 Hz, 1H), 8.12 (d, J=9.0 Hz, 1H), 8.27 (d, J=9.0 Hz, 1H), 8.60 (s, 1H), 9.14–9.37 (bs, 2H), 12.71–13.25 (bs, 1H); IR (neat) 2520–3100, 1715, 1685, 1630, 1600, 1575, 1510, 1485, 1455, 1295, 1270, 1265, 1210, 1200, 1165, 1110, and 1100 cm$^{-1}$; mass spectrum [(+) ESI], m/z 406 (M +H)$^+$ and [(−) ESI], m/z 404 (M−H)$^-$; Anal. Calcd. for $C_{21}H_{18}F_3NO_4 \cdot HCl \cdot 0.1H_2O$: C, 56.86; H, 4.36; N, 3.16, Found: C, 56.45; H, 4.18; N, 3.09.

EXAMPLE 2

5-{[(4-Fluorobenzyl)amino]methyl)-6-methoxy-2-naphthoic acid

The title compound was prepared as a white solid (0.212 g, 34% for two steps) from 6-methoxy-5-formyl-2-naphthoic acid methyl ester using 4-fluorobenzyl amine and a procedure similar to steps 3–4 of Example 1, mp 268–270° C. (decomp.); $^1$H NMR (DMSO-$d_6$) δ3.94 (s, 3H), 4.29 (s, 2H), 4.48 (s, 2H), 7.31 (t, J=8.9 Hz, 2H), 7.60 (d, J=9.2 Hz, 1H), 7.65 (dd, J=5.7, 8.6 Hz, 2H), 7.99 (dd, J=1.5, 8.9 Hz, 1H), 8.12 (d, J=9.0 Hz, 1H), 8.28 (d, J=9.2 Hz, 1H), 8.60 (d, J=0.92 Hz, 1H), 9.07–9.42 (bs, 2H), 12.73–13.27 (bs, 1H); IR (neat) 3470, 3390, 2880–3080, 2820, 2760, 2680, 2610, 1710, 1630, 1600, 1595, 1515, 1485, 1465, 1445, 1270, 1260, 1235, 1210, 1195, 1185, 1095, and 1000 cm$^{-1}$; mass spectrum [(+) ESI], m/z 340 (M +H)$^+$ and [(−) ESI], m/z 338 (M−H)$^-$; Anal. Calcd. for $C_{20}H_{18}FNO_3 \cdot HCl \cdot 0.5H_2O$: C, 62.42; H, 4.98; N, 3.64, Found: C, 62.07; H, 5.37; N, 3.53.

EXAMPLE 3

5-({[4-(Aminosulfonyl)benzyl]amino}methyl)-6-methoxy-2-naphthoic acid

The title compound was prepared as a white solid (0.245 g, 34% for two steps) from 6-methoxy-5-formyl-2-naphthoic acid methyl ester using p-aminomethyl-benzenesulfonamide hydrochloride and a procedure similar to steps 3–4 of Example 1, mp 283–285° C. (decomp.); $^1$H NMR (DMSO-$d_6$) δ3.94 (s, 3H), 4.37 (s, 2H), 4.53 (s, 2H), 7.46 (s, 2H), 7.60 (d, J=9.2 Hz, 1H), 7.77 (d, J=8.2 Hz, 2H), 7.90 (d, J=8.2 Hz, 2H), 8.01 (dd, J=1.4, 9.0 Hz, 1H), 8.16 (d, J=9.0 Hz, 1H), 8.28 (d, J=9.2 Hz, 1H), 8.61 (s, 1H), 9.25–9.46 (bs, 2H), 12.78–13.18 (bs, 1H); IR (neat) 2380–3300, 1670, 1625, 1600, 1485, 1470, 1455, 1430, 1420, 1325, 1310, 1285, 1265, 1220, 1185, 1165, 1105, and 1040 cm$^{-1}$; mass spectrum [(+) ESI], m/z 401 (M+H)$^+$ and [(−) ESI], m/z 399 (M−H)$^-$; Anal. Calcd. for $C_{20}H_{20}N_2O_5S \cdot HCl$: C, 54.98; H, 4.84; N, 6.41, Found: C, 54.60; H, 4.93; N, 6.17.

EXAMPLE 4

5-({[4-(Dimethylamino)benzyl]amino}methyl)-6-methoxy-2-naphthoic acid

The title compound was prepared as a white solid (0.160 g, 23% for two steps) from 6-methoxy-5-formyl-2-naphthoic acid methyl ester using p-dimethylamino-benzyl amine dihydrochloride and a procedure similar to steps 3–4 of Example 1, mp >215° C. (decomp.); $^1$H NMR (DMSO-$d_6$) δ2.97 (s, 6H), 3.94 (s, 3H), 4.14–4.23 (m, 2H), 4.39–4.48 (m, 2H), 6.88–7.14 (bs, 2H), 7.47 (d, J=8.0 Hz, 2H), 7.59 (d, J=9.3 Hz, 1H), 7.97 (dd, J=1.7, 8.9 Hz, 1H), 8.06 (d, J=9.0 Hz, 1H), 8.26 (d, J=9.2 Hz, 1H), 8.59 (d, J=1.6 Hz, 1H), 9.05–9.24 (bs, 2H), 11.90–13.75 (bs, 1H); IR (neat) 3320, 2330–3130, 1705, 1670, 1625, 1580, 1515, 1485, 1460, 1430, 1280, 1260, 1220, 1200, 1175, and 1100 cm$^{-1}$; mass spectrum [(+) ESI], m/z 365 (M +H)$^+$ and [(−) ESI], m/z 363 (M−H)$^-$; Anal. Calcd. for $C_{22}H_{24}N_2O_3 \cdot 2HCl \cdot 1.25H_2O$: C, 57.46; H, 6.25; N, 6.09, Found: C, 57.25; H, 6.37; N, 5.93.

EXAMPLE 5

6-(Carboxymethoxy)-5-({[4-(trifluoromethoxy)benzyl]amino}methyl)-2-naphthoic acid step 1

6-Hydroxy-2-naphthoic acid methyl ester

The title compound was prepared as a solid (4.67 g, 87%) from 6-hydroxy-2-naphthoic acid using a procedure similar to step 1 of Example 1; $^1$H NMR (DMSO-$d_6$) δ3.86 (s, 3H), 7.12–7.19 (m, 2H), 7.75 (d, J=8.7 Hz, 1H), 7.84 (dd, J=1.7, 8.6 Hz, 1H), 7.96 (d, J=8.8 Hz, 1H), 8.47 (d, J=0.8 Hz, 1H), 10.17 (s, 1H); mass spectrum [(+) ESI], m/z 203 (M+H)$^+$ and [(−) ESI], m/z 201 (M−H)$^-$.

step 2

6-Methoxycarbonylmethoxy-2-naphthoic acid methyl ester

To a stirred solution of 6-hydroxy-2-naphthoic acid methyl ester (0.500 g, 2.47 mmol) in acetone (25 mL) at rt was added $Cs_2CO_3$ (0.886 g, 2.72 mmol) followed by methyl bromoacetate (0.257 mL, 2.72 mmol) dropwise. After 18 h at this temperature, it was diluted with EtOAc (200 mL). This layer was washed with 1 N HCl (20 mL), sat. aq. $NaHCO_3$ (20 mL), and brine (20 mL) and then dried ($MgSO_4$). After concentration, the residue was recrystallized from MeOH:$H_2O$ to afford the product (0.573 g, 85%) as a solid; $^1$H NMR (DMSO-$d_6$) δ3.71 (s, 3H), 3.87 (s, 3H), 4.95 (s, 2H), 7.30 (dd, J=2.6, 8.9 Hz, 1H), 7.38 (d, J=2.4 Hz, 1H), 7.87 (d, J=8.7 Hz, 1H), 7.92 (dd, J=1.6, 8.6 Hz, 1H), 8.06 (d, J=9.1 Hz, 1H), 8.55 (s, 1H); mass spectrum [(+) ESI], m/z 275 (M+H)$^+$.

step 3

6-Methoxycarbonylmethoxy-5-formyl-2-naphthoic acid methyl ester

The title compound was prepared as a solid (0.065 g, 11%) from 6-methoxycarbonylmethoxy-2-naphthoic acid methyl ester using a procedure similar to step 2 of Example 1; $^1$H NMR (DMSO-$d_6$) δ3.71 (s, 3H), 3.89 (s, 3H), 5.22 (s, 2H), 7.63 (d, J=9.3 Hz, 1H), 8.10 (dd, J=1.9, 9.1 Hz, 1H), 8.47 (d, J=9.2 Hz, 1H), 8.64 (d, J=1.9 Hz, 1H), 9.15 (d, J=9.0 Hz, 1H), 10.82 (s, 1H); mass spectrum [(+) ESI], m/z 303 (M+H)$^+$, 325 (M+Na)$^+$.

step 4

6-(Carboxymethoxy)-5-({[4-(trifluoromethoxy)benzyl]amino}methyl)-2-naphthoic acid The title compound was prepared as a white solid (0.050 g, 58% for two steps) from 6-methoxycarbonylmethoxy-5-formyl-2-naphthoic acid methyl ester using 4-trifluoromethoxy-benzyl amine and a procedure similar to steps 3–4 of Example 1, mp >266° C. (decomp.); $^1$H NMR (DMSO-$d_6$) δ4.31 (s, 2H), 4.58 (s, 2H), 4.77 (s, 2H), 7.42 (d, J=8.4 Hz, 2H), 7.62 (d, J=9.3 Hz,1 H), 7.68 (d, J=8.7 Hz, 2H), 8.00 (dd, J=1.5, 8.9 Hz, 1H), 8.17 (d, J=9.0 Hz, 1H), 8.21 (d, J=9.3 Hz, 1H), 8.58 (d, J=1.2 Hz, 1H), 10.05–10.54 (bs, 1H), 12.74–13.46 (bs, 1H); IR (neat) 2450–3200, 1695, 1630, 1600, 1575, 1510, 1485, 1440, 1310, 1265, 1215, 1170, and 1110 cm$^{-1}$; mass spectrum [(+) ESI], m/z 450 (M+H)$^+$ and [(−) ESI], m/z 448 (M−H)$^-$; Anal. Calcd. for $C_{22}H_{18}F_3NO_6 \cdot 1.0H_2O$: C, 56.54; H, 4.31; N, 3.00, Found: C, 56.16; H, 4.26; N, 2.86.

What is claimed is:

1. Compounds of Formula I:

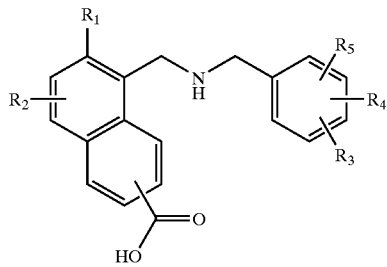

wherein:

$R_1$ is hydroxyl, alkoxy of 1–4 carbons, or —O(CH$_2$)$_n$X;

n is an integer of 1–3;

X is CONHR$_6$ or CO$_2$R$_6$;

$R_2$ is hydrogen, halogen, hydroxyl, alkyl of 1–4 carbons, alkoxy of 1–4 carbons, or acyl of 1–4 carbons;

$R_3$, $R_4$ and $R_5$ are each independently, hydrogen, halogen, hydroxyl, alkyl of 1–4 carbons, alkoxy of 1–4 carbons, acyl of 1–4 carbons, CF$_3$, OCF$_3$, SO$_2$NHR$_6$, NR$_6$R$_7$ or CO$_2$R$_6$;

$R_6$, and $R_7$ are each, independently, hydrogen, alkyl of 1–4 carbons, or alkylaryl where the aryl group is substituted with $R_2$;

or a pharmaceutically acceptable salt thereof.

2. Compounds of Formula II:

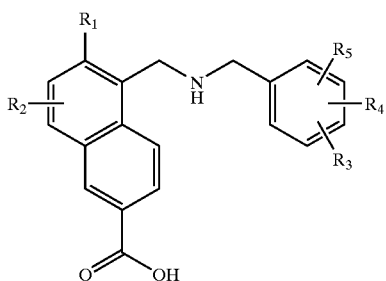

wherein:

$R_1$ is hydroxyl, alkoxy of 1–4 carbons, or —O(CH$_2$)$_n$X;

n is an integer of 1–3;

X is CONHR$_6$ or CO$_2$R$_6$;

$R_2$ is hydrogen, halogen, hydroxyl, alkyl of 1–4 carbons, alkoxy of 1–4 carbons, or acyl of 1–4 carbons;

$R_3$, $R_4$ and $R_5$ are each independently, hydrogen, halogen, hydroxyl, alkyl of 1–4 carbons, alkoxy of 1–4 carbons, acyl of 1–4 carbons, CF$_3$, OCF$_3$, SO$_2$NHR$_6$, NR$_6$R$_7$ or CO$_2$R$_6$;

$R_6$, and $R_7$ are each, independently, hydrogen, alkyl of 1–4 carbons, or alkylaryl where the aryl group is substituted with $R_2$;

or a pharmaceutically acceptable salt thereof.

3. Compounds of Formula III:

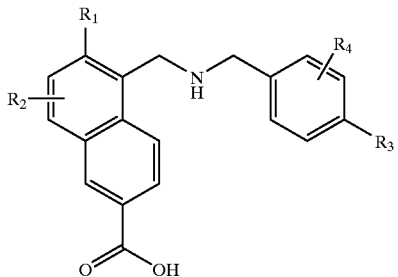

wherein:

$R_1$ is hydroxyl, alkoxy of 1–4 carbons, or —O(CH$_2$)$_n$CO$_2$R$_5$;

n is an integer of 1–3;

$R_2$ is hydrogen, halogen, hydroxyl, alkyl of 1–4 carbons, alkoxy of 1–4 carbons, or acyl of 1–4 carbons;

$R_3$, $R_4$, are each, independently, hydrogen, halogen, hydroxyl, alkyl of 1–4 carbons, alkoxy of 1–4 carbons, acyl of 1–4 carbons, CF$_3$, OCF$_3$, SO$_2$NHR$_5$, NR$_5$R$_6$, or CO$_2$R$_5$;

$R_5$, $R_6$ are each, independently, hydrogen, alkyl of 1–4 carbons, or alkylaryl where aryl group is substituted with $R_2$;

or a pharmaceutically acceptable salt thereof.

4. The compound of claim 1, which is 6-Methoxy-5-({[4-(trifluoromethoxy)benzyl]amino}methyl)-2-naphthoic acid.

5. The compound of claim 1, which is 5-{[(4-Fluorobenzyl)amino]methyl}-6-methoxy-2-naphthoic acid.

6. The compound of claim 1, which is 5-({[4-(Aminosulfonyl)benzyl]amino}methyl)-6-methoxy-2-naphthoic acid.

7. The compound of claim 1, which is 5-({[4-(Dimethylamino)benzyl]amino}methyl)-6-methoxy-2-naphthoic acid.

8. The compound of claim 1, which is 6-(Carboxymethoxy)-5-({[4-(trifluoromethoxy)benzyl]amino}methyl)-2-naphthoic acid.

9. A method of treating metabolic disorders mediated by insulin resistance or hyperglycemia in a mammal in need thereof which comprises administering to said mammal, a therapeutically effective amount of a compound of Formula I:

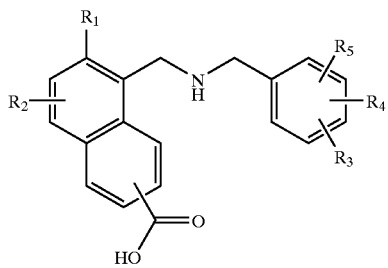

wherein:

$R_1$ is hydroxyl, alkoxy of 1–4 carbons or —O(CH$_2$)$_n$X;

n is an integer of 1–3;

X is CONHR$_6$, or CO$_2$R$_6$;

$R_2$ is hydrogen, halogen, hydroxyl, alkyl of 1–4 carbons, alkoxy of 1–4 carbons or acyl of 1–4 carbons;

$R_3$, $R_4$ and $R_5$ are each independently, hydrogen, halogen, hydroxyl, alkyl of 1–4 carbons, alkoxy of 1–4 carbons, acyl of 1–4 carbons, $CF_3$, $OCF_3$, $SO_2NHR_6$, $NR_6R_7$ or $CO_2R_6$;

$R_6$, and $R_7$ are each, independently, hydrogen, alkyl of 1–4 carbons, or alkylaryl where the aryl group is substituted with $R_2$;

or a pharmaceutically acceptable salt thereof.

10. A method of treating or inhibiting type II diabetes in a mammal in need thereof which comprises administering to said mammal a therapeutically effective amount of compound of Formula I:

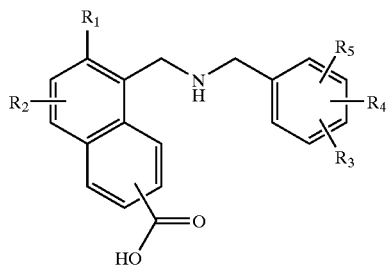

wherein:

$R_1$ is hydroxyl, alkoxy of 1–4 carbons or —O(CH$_2$)$_n$X;

n is an integer of 1–3;

X is CONHR$_6$ or CO$_2$R$_6$;

$R_2$ is hydrogen, halogen, hydroxyl, alkyl of 1–4 carbons, alkoxy of 1–4 carbons, or acyl of 1–4 carbons;

$R_3$, $R_4$ and $R_5$ are each, independently, hydrogen, halogen, hydroxyl, alkyl of 1–4 carbons, alkoxy of 1–4 carbons, acyl of 1–4 carbons, $CF_3$, $OCF_3$, $SO_2NHR_6$, $NR_6R_7$ or $CO_2R_6$;

$R_6$, and $R_7$ are each independently, hydrogen, alkyl of 1–4 carbons, or alkylaryl where the aryl group is substituted with $R_2$;

or a pharmaceutically acceptable salt thereof.

11. A method of modulating glucose levels in a mammal in need thereof which comprises administering to said mammal a therapeutically effective amount of a compound of Formula I:

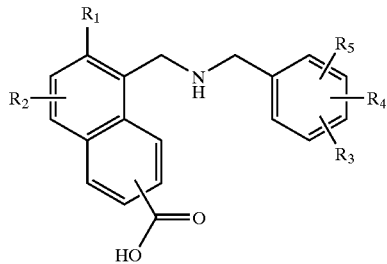

wherein:

$R_1$ is hydroxyl, alkoxy of 1–4 carbons, or —O(CH$_2$)$_n$X;

n is an integer of 1–3;

X is CONHR$_6$ or CO$_2$R$_6$;

$R_2$ is hydrogen, halogen, hydroxyl, alkyl of 1–4 carbons, alkoxy of 1–4 carbons or acyl of 1–4 carbons;

$R_3$, $R_4$ and $R_5$ are each independently, hydrogen, halogen, hydroxyl, alkyl of 1–4 carbons, alkoxy of 1–4 carbons, acyl of 1–4 carbons, $CF_3$, $OCF_3$, $SO_2NHR_6$, $NR_6R_7$ or $rCO_2R_6$;

$R_6$, and $R_7$ are each independently, hydrogen, alkyl of 1–4 carbons, or alkylaryl where the aryl group is substituted with $R_2$;

or a pharmaceutically acceptable salt thereof.

12. A pharmaceutical composition which comprises a compound of Formula I:

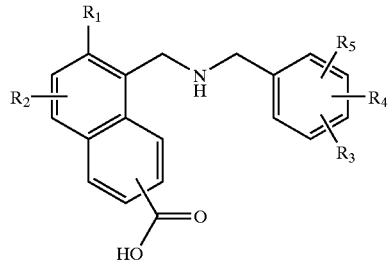

wherein:

$R_1$ is hydroxyl, alkoxy of 1–4 carbons, or —O(CH$_2$)$_n$X;

n is an integer of 1–3;

X is CONHR$_6$, or CO$_2$R$_6$;

$R_2$ is hydrogen, halogen, hydroxyl, alkyl of 1–4 carbons, alkoxy of 1–4 carbons, or acyl of 1–4 carbons;

$R_3$, $R_4$, and $R_5$ are each independently, hydrogen, halogen, hydroxyl, alkyl of 1–4 carbons, alkoxy of 1–4 carbons, acyl of 1–4 carbons, $CF_3$, $OCF_3$, $SO_2NHR_6$, $NR_6R_7$, or $CO_2R_6$;

$R_6$, and $R_7$ are each independently, hydrogen, alkyl of 1–4 carbons, or alkylaryl where the aryl group is substituted with $R_2$;

or a pharmaceutically acceptable salt thereof, and a pharmaceutical carrier.

* * * * *